(12) United States Patent
Pasij

(10) Patent No.: US 6,726,644 B1
(45) Date of Patent: Apr. 27, 2004

(54) KNEE BRACE

(76) Inventor: Peter Pasij, 725 Indiana St., Elmhurst, IL (US) 60126

(*) Notice: Subject to any disclaimer, the term of this patent is extended or adjusted under 35 U.S.C. 154(b) by 0 days.

(21) Appl. No.: 10/462,470

(22) Filed: Jun. 17, 2003

(51) Int. Cl.[7] .................................................. A61F 5/00
(52) U.S. Cl. ............................................ 602/23; 602/26
(58) Field of Search ................................. 128/845, 869, 128/882, 883; 602/23, 26, 60–65

(56) References Cited

U.S. PATENT DOCUMENTS

| | | | | |
|---|---|---|---|---|
| 4,295,683 A | * | 10/1981 | Dubbink | 297/377 |
| 4,664,118 A | * | 5/1987 | Batters | 128/802 |
| 4,782,918 A | * | 11/1988 | Brunner | 182/187 |
| 5,038,761 A | * | 8/1991 | Richardson | 128/80 C |

* cited by examiner

Primary Examiner—Michael A. Brown
(74) Attorney, Agent, or Firm—Kajane McManus

(57) ABSTRACT

The brace includes, a body having a layer of mesh like breathable material having a light weight aluminum border on an outer surface thereof. Hook and loop straps with an elasticized center area are used to engage the brace about the knee joint and a slidable sleeve is provided to cover a portion of the hook and loop strap in the area behind the knee.

8 Claims, 2 Drawing Sheets

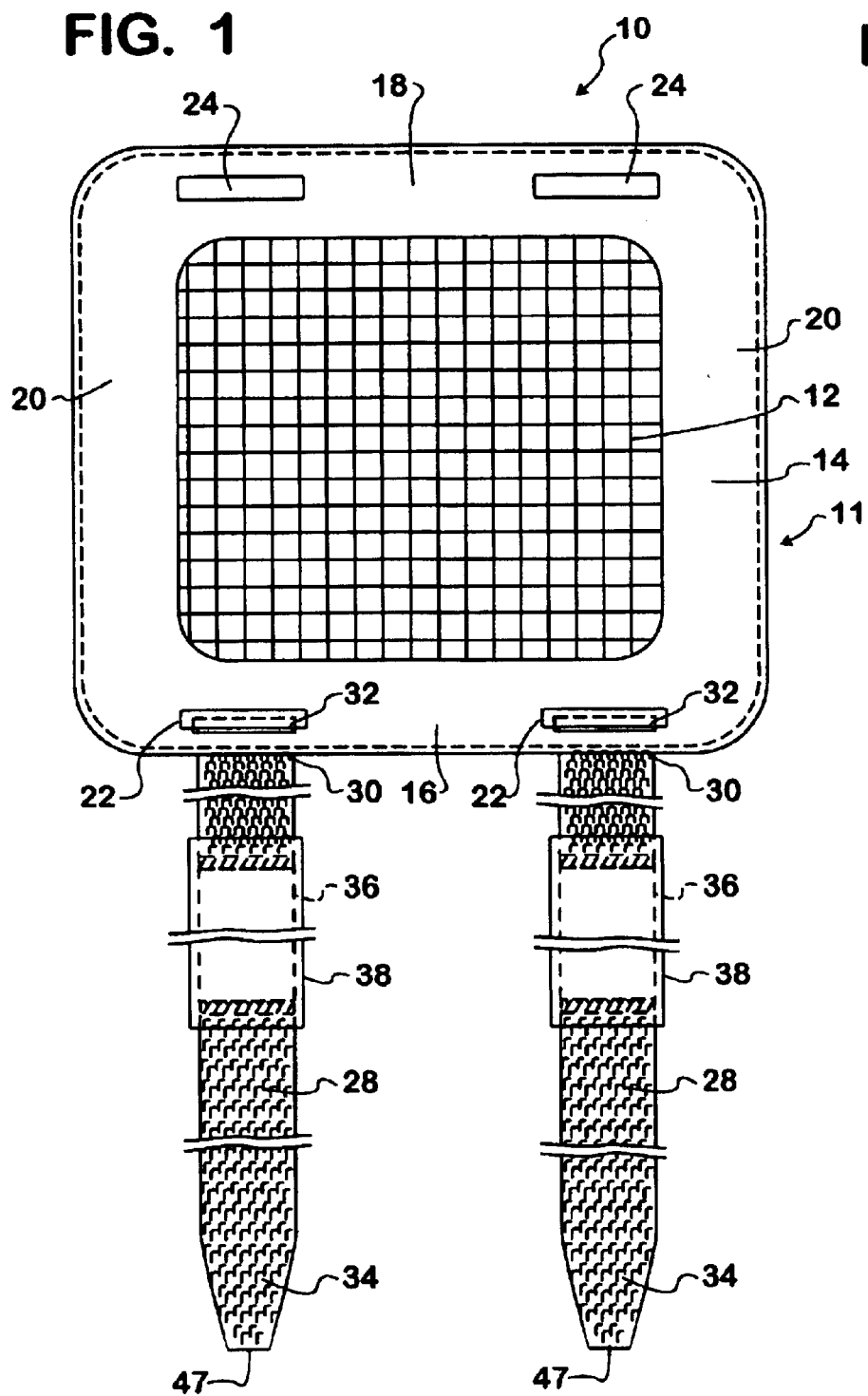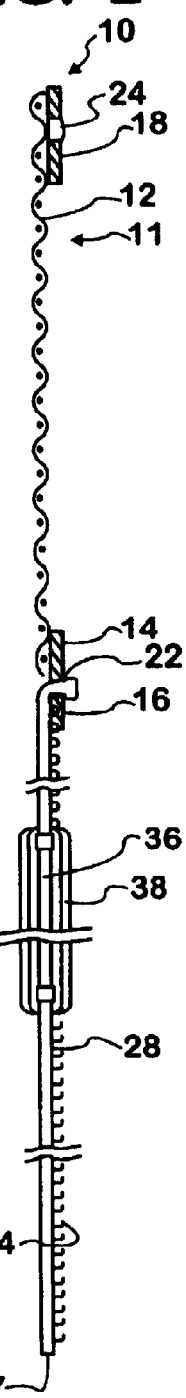

KNEE BRACE

BACKGROUND OF THE INVENTION

1. Field of the Invention

The present invention relates to a knee brace. More specifically, the knee brace is particularly useful after knee replacement surgery to stabilize the joint and significantly reduce, if not eliminate, pain associated with such procedure. The brace is light, flexible, and caused virtually no sweating.

2. Prior Art

Heretofore various knee braces have been proposed. However, most are cumbersome, tight, restrictive and cause excessive sweating in the area underlying the brace.

Such disadvantages are overcome by the brace of the present invention.

SUMMARY OF THE INVENTION

According to the present invention there is provided a knee brace comprising a body having a layer of mesh like breathable material having a light weight aluminum border on an outer surface thereof and hook and loop straps for engaging the brace about a knee joint.

BRIEF DESCRIPTION OF THE DRAWINGS

FIG. 1 is a top plan view of the brace of the present invention.

FIG. 2 is a sectional side view of the brace of FIG. 1.

DESCRIPTION OF THE PREFERRED EMBODIMENT

Figure 3:
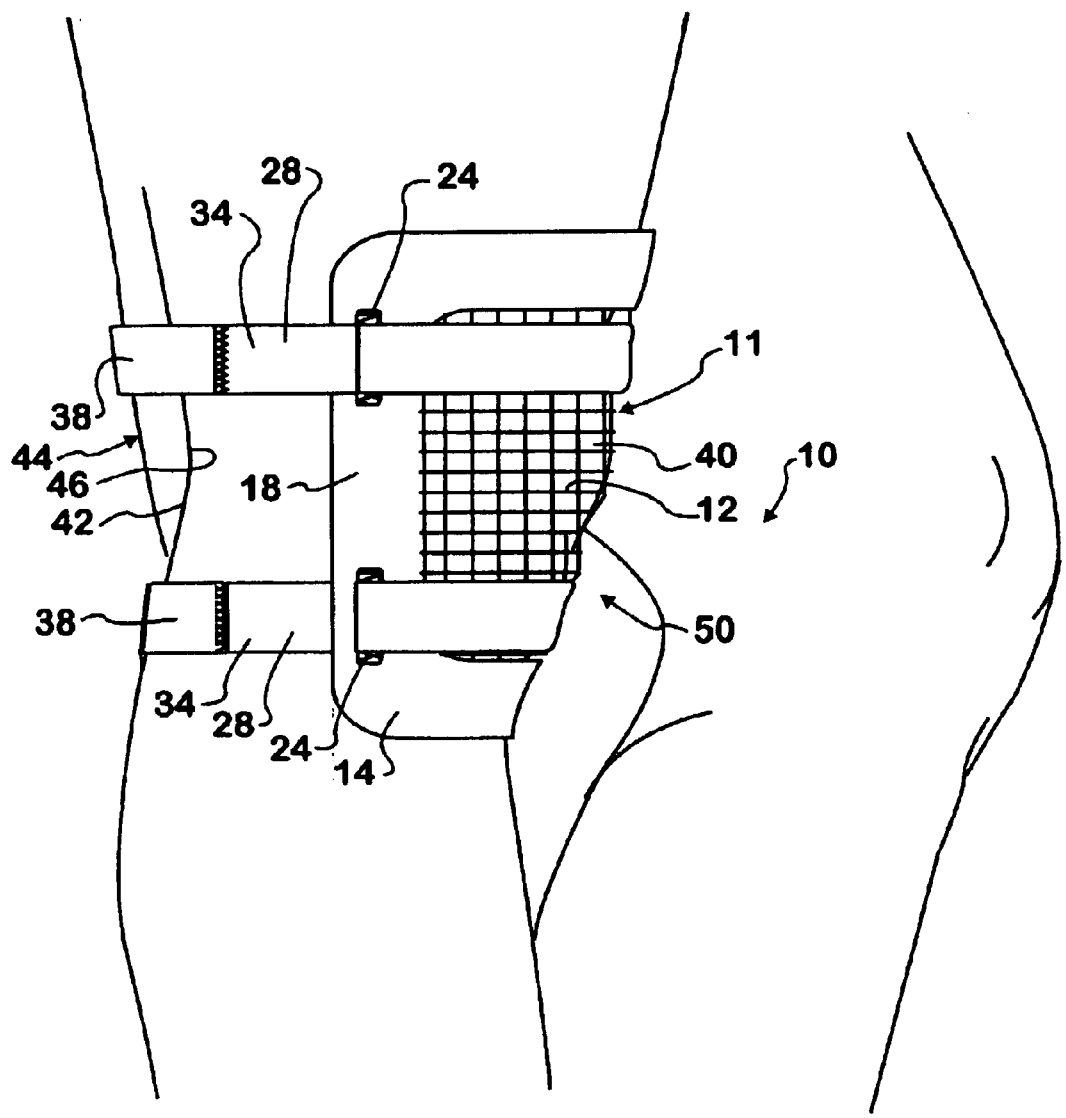
FIG. 3 shows the brace in use positioned about a knee joint.

Referring now to the drawings in greater detail there is illustrated therein a knee brace made in accordance with the teachings of the present invention and generally identified by the reference numeral 10.

As shown, in a preferred embodiment the brace approximates a square body 11 of the breathable mesh material 12 which is surrounded by a border of light weight flexible metal 14, such as thin aluminum, with the metal surrounded center area of mesh material 12 being open to the environment, so no sweat is produced therebeneath.

The brace has two side edges 16 and 18 and mirror image top and bottom edges 20.

Along each side edge 16 and 18 are provided a pair of slits 22 and 24. Through each of the pair of slits 22 is received a hook and loop material strap 28 having one end 30 having a stop 32 thereon which cannot slide through the slit 22. The remainder of each of the hook and loop strap 28 extends laterally from the body 11, with the hook and loop surface 34 thereof facing away from the mesh material 12 layer. Each strap 28 includes an elasticized centered area 36 for accommodating knee joints of varied girth.

Each strap 28 also incorporates a sleeve 38, preferably also of mesh material 12, which slides therealong and aligns behind the knee joint, to keep the skin from sweating or being chafed by the strap 28.

In the preferred embodiment, the brace body 11 is approximately 4.5 inches wide and approximately 5 inches high with the straps 28 being approximately 1 inch wide and 18 inches in length with the elastic portion thereof being approximately 3.5 inches long and each sleeve 38 being approximately 4 inches in length, though this should not be construed as limiting.

Also, the metal material 14 is preferably aluminum of 20 thousandths inch in thickness and the mesh is approximately 0.25 inch thick, though this should not be construed as limiting.

In use, as shown in FIG. 3, a user places the body 11 if the brace 10 over the kneecap 40, takes a lower one of the straps 28, and pulls it around the back 42 of the knee 44, placing same below the crease 46, with the sleeve 38 being centered behind the joint, pulls a free end 47 of the strap 28 through the corresponding slit 24 on side edge 18, pulls the strap across the body 11 of the brace 10 and engages the free end 47 to the strap 28 along the side 16 of the brace 10.

The same technique is used for engaging the upper strap 28, except that the upper strap 28 is positioned above the crease 46 in the back 42 of the knee 44.

Thusly, the engaged brace 10 is easy to use, stabilized the knee joint 50, is not visible under slack, does not cause sweating, is not cumbersome or restrictive, is light, flexible, accommodating and breathable.

As described above, the brace 10 provides a number of advantages, some of which have been described above and others of which are inherent in the invention. Also, modifications may obviously be proposed to the disclosed preferred embodiment, which should not be construed as limiting, with any such proposed modifications considered to be within the scope of the invention, the scope only to be limited as necessitated by the accompanying claims.

What is claimed is:

1. A knee brace comprising a body having a layer of mesh breathable material having a light weight aluminum border on an outer surface thereof and hook and loop straps for engaging the brace about a knee joint.

2. The brace of claim 1 wherein the straps include an elasticized center area.

3. The brace of claim 1 further including a slidable sleeve for covering a portion of the hook and loop strap in the area behind the knee.

4. The brace of claim 1 wherein the mesh is preferably approximately 0.25 inch thick.

5. The brace of claim 1 wherein the aluminum is preferably approximately 20 thousandths inch thick.

6. The brace of claim 1 wherein the body is approximately 4.5 inches wide and approximately 5 inches high.

7. The brace of claim 1 wherein the straps are approximately 18 inches long.

8. The brace of claim 1 wherein each strap is engaged to the body and engages itself once wound around the knee joint.

\* \* \* \* \*